United States Patent [19]

Bauer

[11] 4,190,419

[45] Feb. 26, 1980

[54] DEVICE FOR DETECTING SERUM BILIRUBIN

[75] Inventor: Robert Bauer, Bristol, Ind.

[73] Assignee: Miles Laboratories, Inc., Elkhart, Ind.

[21] Appl. No.: 944,718

[22] Filed: Sep. 22, 1978

[51] Int. Cl.$^2$ .................... G01N 31/22; G01N 33/16
[52] U.S. Cl. ................... 23/230 B; 23/905; 252/408; 422/56
[58] Field of Search ............... 23/230 B, 905; 422/56; 252/408

[56] References Cited

U.S. PATENT DOCUMENTS

| | | | |
|---|---|---|---|
| 3,585,001 | 6/1971 | Mast | 23/230 B |
| 4,038,031 | 7/1977 | Lam | 23/230 B |
| 4,078,892 | 3/1978 | Steinbrink, Jr. | 23/230 B |

*Primary Examiner*—Sidney Marantz
*Attorney, Agent, or Firm*—Charles J. Herron

[57] ABSTRACT

A test device for detecting bilirubin in serum is provided which comprises a carrier and, incorporated therewith, a composition comprising a diazonium salt, p-toluenesulfonic acid and dyphylline. The test device is free of the undesirable characteristic of nonuniformity of color development when reacted with a test sample. Uniform color development provides a more accurate and reliable quantitation of serum bilirubin. A method of making and a method of using the device are likewise disclosed.

10 Claims, No Drawings

DEVICE FOR DETECTING SERUM BILIRUBIN

FIELD OF THE INVENTION

The present invention provides an improved test device, method of making the device and method for the detection of bilirubin in serum. More particularly, a composition is provided which, when incorporated with a carrier to form a device, allows color to develop uniformly on the test device.

BACKGROUND OF THE INVENTION

In the breakdown of heme, bile pigments, principally bilirubin, are produced in the serum which are then removed by the liver. The amount of bile pigments formed each day is closely related to the amount of hemoglobin destroyed and liver function. It is estimated that 1 gram (g) of hemoglobin yields 35 milligrams (mg) of bilirubin. Normally 0.1 to 1.5 mg of bilirubin is present in 100 milliliters (ml) of human plasma or serum.

Estimation of serum bilirubin has been recognized to be of great value in clinical studies, such as of liver dysfunction. A method for quantitatively assaying the bilirubin content of the serum was first devised by Van den Bergh by application of Ehrlich's test for bilirubin in urine. The Ehrlich reaction is based on the coupling of diazotized sulfanilic acid (Ehrlich's diazo reagent) and bilirubin to produce a reddish-purple azo compound. In the original procedure as described by Ehrlich, alcohol was used to provide a solution in which both bilirubin and the diazo reagent were soluble. Van den Bergh discovered that by omitting the alcohol when assaying for bile pigment in human bile normal development of the color occurred "directly", that is, without the addition of alcohol. This form of bilirubin which would react without the addition of alcohol was thus termed "direct-reacting." However, it was still necessary to add alcohol to detect bilirubin in normal serum. To that form of bilirubin which could be measured only after the addition of alcohol the term "indirect-reacting" was applied.

The indirect bilirubin is "free" (unconjugated) bilirubin en route to the liver from the reticuloendothelial tissues where the bilirubin is produced by the breakdown of heme porphyrins. Since this bilirubin is not water-soluble it requires addition of alcohol to initiate coupling with the diazo reagent. In the liver the free bilirubin becomes conjugated with glucuronic acid. Conjugated bilirubin, being water-soluble, can react directly with the diazo reagent so the the "direct bilirubin" of Van den Bergh is actually a bilirubin conjugate (bilirubin glucuronide).

Sulfonic acids other than sulfanilic acid have been suggested as acceptable in the diazo coupling reaction described. Such include p-toluenesulfonic acid, sulfosalicylic acid, sulfonic acid and hexamic acid. See, for example, U.S. Pat. No. 3,585,001.

It has also been known that other substances besides alcohol exhibit the same influence, that is of enhancing the diazo coupling of "free" bilirubin, allowing for a measure of indirect, and thus total, bilirubin. These substances are referred to as "accelerating agents" and have included caffeine, dyphylline, sodium acetate, sodium benzoate, gum arabic and others. Reference is made to Henry, R. J., Clinical Chemistry, Principles and Technics, Second Edition, Harper and Row, pp. 1047 (1974); With, T.K., Bile Pigments, Academic Press, pp. 324-327 (1968); and U.S. Pat. No. 4,038,031.

Test devices for bilirubin determination, such as in strip format, have been disclosed which make use of the diazo coupling reaction. See, for example, the above-identified patents as well as U.S. Pat. Nos. 3,853,476; 3,880,588; 3,912,457; 4,069,016; and 4,069,017. These devices have served a useful purpose in clinical diagnosis.

It has now been recognized, however, that these prior art devices suffer from the drawback that they do not absorb serum specimens in a uniform manner. The color formed at the point of sample application is quite intense, whereas very little, if any, color is developed peripheral to this point. This non-uniformity is a particularly undesirable characteristic, since uniform color development is necessary to achieve the precision required for a quantitative test.

This problem in prior art devices has, in accordance with the invention, been recognized and overcome as is fully described below.

SUMMARY OF THE INVENTION

It has now been found that a test device for detecting bilirubin in serum which comprises a carrier and, incorporated therewith, a composition comprising a diazonium salt, p-toluenesulfonic acid and dyphylline is free of the undesirable characteristic of nonuniformity of color development when reacted with a test sample. The presence of bilirubin in a serum sample is detected by a method which comprises contacting the device according to the invention with the sample to be tested and observing any resultant colorimetric response. The test device is prepared by a method which comprises incorporating, such as by saturation with an impregnating solution, a carrier with a composition as described above.

The difficulties of nonuniformity which have now been overcome are believed to have been a result of serum protein precipitation in the prior art test devices. This theory is not, however, one on which the invention is necessarily predicated.

Notwithstanding the ability of the p-toluenesulfonic acid to produce a pH sufficiently low to stabilize the diazonium compound, it is now possible by using the test device according to the invention to obtain uniform color development in response to serum bilirubin. As a result, highly quantitative instrumental reflectance values, corresponding to bilirubin concentration, can be obtained independent of the point of application of the serum sample to the test device.

DESCRIPTION OF THE PREFERRED EMBODIMENTS

Specific terms used in the following description are intended to refer only the particular embodiments selected for illustration of the invention defined by the claims.

Test devices intended for detection of serum bilirubin can use any aromatic diazonium salt which exclusively or preponderantly contains electron-attracting groups. Thus, for example, in the benzene series, the substituents can be nitro groups, halogen atoms, carboxyl groups, sulfonic acid residues, nitrile groups or quaternary ammonium groups. Electron-donating groups, for example alkoxy radicals, can also be present to a limited extent. Furthermore, diazotized naphthylamine and benzidine derivatives can also be used. Less suitable are benzene-diazonium salts which exclusively contain electron-donating groups, such as alkoxy, alkyl or arylamino radicals, because these react comparatively slowly with bilirubin.

Such diazonium salts can be added directly or can be formed in situ by the reaction of members of the aniline series with a nitrite, such as is shown in the Example. Whether the diazonium salt is added directly as the salt, itself, or the salt is formed in situ, the diazonium salts of substituted and unsubstituted halobenzenes, particularly 2,4-dichlorobenzene, are preferred. Also, diazonium salts of nitro-substituted benzenes, such as p-nitrobenzene diazonium tetrafluoroborate are advantageously selected.

The diazonium salts are present in the impregnation solution in concentrations of from about 0.02 grams/deciliter (g/dl) to about 2.0 g/dl, and preferably from about 0.05 g/dl to about 0.5 g/dl. The p-toluenesulfonic acid is used in the impregnation solution in concentrations of from about 0.5 g/dl to about 10.0 g/dl and preferably from about 1.0 g/dl to about 6.0 g/dl. The dyphylline is used in the impregnation solution in concentrations of from about 6.0 g/dl to about 14.0 g/dl, and preferably from about 8.0 g/dl to about 12.0 g/dl. The solvent used in preparing the impregnation solutions can be water, physiological solutions, suitable organic solvents or mixtures thereof. Various additional components can optionally be added. Such can include Gantrez AN-139 (a copolymer of methyl vinyl ether and maleic anhydride from GAF Corp., Chemical Products, N.Y., N.Y.). The reaction is preferably carried out at a relatively acid pH, such as from about pH 1 to about pH 5.

Test devices of the invention are prepared by a method which comprises incorporating a carrier, such as a bibulous matrix, with the test composition. When this incorporation is by saturation with an impregnation solution, as previously defined, of the composition, the carrier so impregnated is then dried. In addition to impregnation, the devices of the present invention can be made by other suitable techniques such as printing or spraying the composition onto a substrate or matrix.

The term carrier is envisioned to refer to bibulous and nonbibulous matrices which are insoluble in and maintain their structural integrity when exposed to water or physiological fluids. Suitable bibulous matrices which can be used include paper, cellulose, wood, synthetic resin fleeces, glass fiber, woven and nonwoven fabrics and the like. Nonbibulous matrices include organoplastic materials, such as polypropylene or the like. When a bibulous matrix is employed, the matrix is advantageously affixed by suitable means, such as double-faced adhesive tape, to an insoluble support member, such as an organoplastic strip, e.g. polystyrene, for ease of use.

The test device is advantageously used by dropping a small amount of a test sample thereon or by otherwise introducing a test sample into the carrier matrix, whereby a detectable color change results when bilirubin is present. The test device can be used in the same way whether samples of plasma or serum are tested.

The reacted devices can be read visually, but for more precise quantitation of the concentration of bilirubin detected, colorimetric readings of reacted devices are taken on a reflectance spectrophotometer. Reflectance readings can be obtained from commercially available spectrophotometers such as Beckman DK-2 Spectrophotometer, Beckman Instruments, Inc., Fullerton, California 92634 or Spectrocolorimeter SCF-1, Israel Electro-Optical Industry Ltd. (distributed in the U.S. by Broomer Research Corporation, Plainwell, Long Island, N.Y. 11803).

The illustrative example set forth below will suggest various substitutions and changes to one skilled in the art which are contemplated as within the scope of the claims.

EXAMPLE I

In this example devices prepared according to the invention and devices incorporating other combinations of reagents were compared for uniformity of color development and, thus, reliability of bilirubin concentration data obtained.

Six different impregnation solutions were prepared under ambient laboratory conditions in a solvent of 45.0 milliliters (ml) distilled $H_2O$ and 5.0 ml of a 10 g/dl solution of Gantrez AN-139 according to the formulations set forth in Table 1.

The p-toluenesulfonic acid and sulfosalicylic acid, were purchased from Eastman Organic Chemicals, Rochester, N.Y. 14650. Hexamic acid was obtained from Abbott Laboratories, North Chicago, Illinois. The 1,5-napthalene disulfonic acid, disodium; 2,4-dichloroaniline; and sodium nitrite were standard reagent grade material. Dyphylline and caffeine were purchased from Aldrich Chemical Co., Inc., Milwaukee, Wisconsin 53233.

TABLE I

| Components | A | B | C | D | E | F |
| --- | --- | --- | --- | --- | --- | --- |
| sulfosalicylic acid | — | 3.5 g | — | 3.5 g | — | — |
| hexamic acid | — | — | — | — | 3.0 g | 3.0 g |
| p-toluenesulfonic acid | 2.8 g | — | 2.8 g | — | — | — |
| caffeine | — | 5.0 g | 5.0 g | — | 5.0 g | — |
| dyphylline | 5.0 g | — | — | 5.0 g | — | 5.0 g |
| 1,5-napthalene disulfonic acid, disodium | 0.3 g | 0.3 g | 0.3 g | 0.3 g | 0.3 g | 0.3 g |
| 2,4-dichloroaniline | 0.0375 g | 0.0375 g | 0.0375 g | 0.0375 g | 0.0375 g | 0.0375 g |
| sodium nitrite | 0.10 g | 0.10 g | 0.10 g | 0.10 g | 0.10 g | 0.10 g |

The reagents include 2,4-dichloroaniline and sodium nitrite which interreact in situ in the impregnation solution to form a 2,4-dichlorobenzene diazonium salt, in this case 2,4-dichlorobenzene diazonium 1,5-napthalene disulfonate.

The solution having formulation A was used to prepare devices according to the invention. The solutions having formulations B through F were used to prepare other devices for the comparison. It was immediately observed that formulations C and E, combining caffeine with p-toluenesulfonic acid and hexamic acid, respectively, would not go into solution, and therefore could not even be suitably impregnated into the paper matrices used.

Separate sheets of Eaton-Dikeman 205 filter paper (Eaton-Dikeman, Mount Holly Springs, Pa. 17065)

were impregnated to saturation, each with one of the remaining impregnation solutions identified above. The sheets so impregnated were subjected to 60° C. in a standard laboratory oven until dry. These paper sheets, containing the dried residue of the various impregnation solutions, were then cut to 2.5 millimeters (mm) by 2.5 mm squares to form devices. The devices were then backed by double-faced adhesive tape and fixed thereby to plastic support members. The devices prepared to incorporate compositions having formulations A, B, D and F will be referred to as devices A, B, D and F, respectively.

Serum samples pretested to contain 1 mg/dl of bilirubin were then applied, in volumes of about 30 μl, to different locations (central and peripheral) on each of the devices prepared. Readings of the chromogenic response were taken by reflectance spectrophotometry. The percent reflectance (%R) was read at 560 nanometers (nm) wavelength ninety (90) seconds after sample applications. The results obtained by performance of this experiment are set forth as %R values in Table 2.

TABLE 2

| Sample Position | A | B | C | D | E | F |
|---|---|---|---|---|---|---|
| Central | 49.5 | 47.0 | — | 46.8 | — | — |
| Peripheral | 49.8 | 56.5 | — | 58.2 | — | — |

The %R of device F at 560 nm was so negligible as to be unreadable. It was readable however at 450 nm, which was its reflectance minimum, but readings at this wavelength are subject to variation responsive to the color of the serum itself and thus are unreliable.

The results reported show a %R difference of 0.3 between the devices containing compositions of formulation A to which samples were applied centrally and peripherally. The %R difference between devices containing compositions of formulation B to which samples were applied centrally and perpherally is 9.5. The difference seen between the uniformity of reading in device A versus the nonuniformity of reading in device B is, in this comparison, a ratio of 1 to 31.7. The %R difference between devices containing compositions of formulation D to which samples were applied centrally and peripherally is 11.4. The difference seen between the uniformity of reading in device A versus the nonuniformity of reading in device D is a ratio of 1 to 38. As noted above, no results could even be obtained for devices having compositions with formulations C and E because impregnation solutions could not even be prepared.

The %R readings in Table 2 for the various devices were mathematically extrapolated to bilirubin concentrations expressed as milligrams/deciliter (mg/dl). The %R values reported for device A are very similar and both essentially reflect detection of bilirubin at a concentration of 1.0 mg/dl, the accurate pretested value. The %R values reported for device B, 47.0 and 56.5 respectively, represent 1.0 mg/dl (accurate for the device B formulation) and a false negative (0 mg/dl). The %R values reported for device D represent 1.0 mg/dl and 0 mg/dl bilirubin, respectively. As in device B, substantial variation in bilirubin concentrations detected is observed depending on where on the device the serum was applied.

The experimental results reported and analyzed above clearly indicate that color development is much more uniform and, thus, clinical data much more accurate, when determined using a device of the present invention.

Although the invention has been described with a certain degree of particularity it is understood that numerous changes may be made without departing from the scope of the invention.

What is claimed is:

1. A test device for the detection of bilirubin in a serum sample which device comprises a carrier and, incorporated therewith, a composition comprising a diazonium salt, p-toluenesulfonic acid and dyphylline.

2. The device of claim 1 wherein the diazonium salt is a halobenzene diazonium salt.

3. The device of claim 2 wherein the diazonium salt is 2,4-dichlorobenzene diazonium 1,5-napthalene disulfonate.

4. The device of claim 1 wherein the diazonium salt is a p-nitrobenzene diazonium salt.

5. The device of claim 4 where the p-nitrobenzene diazonium salt is p-nitrobenzene diazonium tetrafluoroborate.

6. A test device for the detection of bilirubin in a serum sample which device comprises a carrier and, incorporated therewith, a composition comprising: p-toluenesulfonic acid; dyphylline, 1,5-napthalene disulfonic acid, disodium; 2,4-dichloroaniline; and sodium nitrite.

7. A method for preparing the test device of claim 1 which comprises contacting a carrier with a composition comprising a diazonium salt, p-toluenesulfonic acid and diphylline.

8. A method for preparing the test device of claim 6 which comprises contacting a carrier with a composition comprising: p-toluenesulfonic acid; dyphylline; 1,5-napthalene disulfonic acid, disodium; 2,4-dichloroaniline; and sodium nitrite.

9. A method for the detection of bilirubin in a serum sample which comprises contacting the device of claim 1 with said sample and observing any resultant colorimetric response.

10. A method for the detection of bilirubin in a serum sample which comprises contacting the device of claim 6 with same sample and observing any resultant colorimetric response.

* * * * *